(12) United States Patent
Li et al.

(10) Patent No.: US 12,173,048 B2
(45) Date of Patent: Dec. 24, 2024

(54) COLLAGEN FIBER-BASED INK AND METHODS OF USE FOR BIOPRINTING

(71) Applicant: Shu-Tung and Alice Li Foundation Inc., Oakland, NJ (US)

(72) Inventors: Shu-Tung Li, Franklin Lakes, NJ (US); Karoly Jakab, Scotch Plains, NJ (US)

(73) Assignee: Shu-Tung and Alice Li Foundation Inc., Oakland, NJ (US)

( * ) Notice: Subject to any disclaimer, the term of this patent is extended or adjusted under 35 U.S.C. 154(b) by 0 days.

(21) Appl. No.: 18/173,506

(22) Filed: Feb. 23, 2023

(65) Prior Publication Data

US 2023/0287085 A1   Sep. 14, 2023

Related U.S. Application Data

(60) Provisional application No. 63/363,324, filed on Apr. 21, 2022, provisional application No. 63/315,750, filed on Mar. 2, 2022.

(51) Int. Cl.
*C07K 14/00* (2006.01)
*A61L 27/24* (2006.01)
*C07K 14/78* (2006.01)

(52) U.S. Cl.
CPC .............. *C07K 14/78* (2013.01); *A61L 27/24* (2013.01)

(58) Field of Classification Search
CPC ................................ C07K 14/78; A61L 27/24
See application file for complete search history.

(56) References Cited

U.S. PATENT DOCUMENTS

| | | | |
|---|---|---|---|
| 2013/0345826 A1 * | 12/2013 | Li | A61L 27/3847 |
| | | | 623/23.58 |
| 2016/0046832 A1 | 2/2016 | Wroblesky et al. | |
| 2018/0353299 A1 | 12/2018 | Wei | |
| 2019/0251217 A1 | 8/2019 | Greyf et al. | |
| 2020/0179563 A1 | 6/2020 | Bagley et al. | |

FOREIGN PATENT DOCUMENTS

EP         4223528 A1 *   8/2023

* cited by examiner

*Primary Examiner* — Jeanette M Lieb
(74) *Attorney, Agent, or Firm* — Fox Rothschild LLP

(57) ABSTRACT

This disclosure provides a collagen fiber-based ink for bioprinting comprising a high solid content of collagen fiber particles that are suitable for manufacturing collagen-based scaffolds and tissue equivalent implants for regenerative medicine applications.

16 Claims, 8 Drawing Sheets

COLLAGEN FIBER-BASED INK AND METHODS OF USE FOR BIOPRINTING

CROSS REFERENCE TO RELATED APPLICATIONS

This application claims priority to U.S. Provisional Application No. 63/315,750 filed on Mar. 2, 2022 and U.S. Provisional Application No. 63/363,324 filed on Apr. 21, 2022. The contents of the applications are incorporated herein by reference in their entireties.

FIELD OF THE INVENTION

This invention relates to collagen fiber-based ink and methods of use for bioprinting.

BACKGROUND OF THE INVENTION

In recent years 3D bioprinting has emerged as an exciting new branch of technology in tissue engineering research and development. Various types of bioprinters have been developed and marketed, which can print certain materials with high precision and accuracy. From the ink material selection point of view, synthetic polymeric materials (e.g., polyethylene glycol and the like) that can form hydrogels with certain rheological properties are suitable for bioprinting. Biopolymeric hydrogel-forming materials for bioprinting include alginate (a negatively charged polysaccharide molecule), chitosan (a positively charged polysaccharide molecule), gelatin (denatured collagen polypeptide molecule), and the like. All these biopolymers can form a hydrogel under certain control conditions of pH and temperature for bioprinting. They are all soluble in aqueous solutions with a concentration defined by the solubility of the material at a given pH, temperature, and ionic strength of the solution.

The primary objective of bioprinting is to print 3D structures of extracellular matrix (ECM) scaffolds and of tissue or organ equivalents that mimic those structures in the body for guiding the body to regenerate its own functional tissues or organs. It is well documented that ECM controls gene expression, i.e., the closer the printed matrix to the body's tissue or organ, the closer function of the new tissue or organ can be regenerated.

Collagen is the major protein in all mammals. Currently, 28 genetically distinct types of collagens have been discovered. It accounts for about 90% of the total proteins in the body. Fiber forming collagens (type I, type II, and type III collagen) are homologous among all mammals, and they account for the majority (90%) of the collagen in the body. They are the major proteins in bone (type I collagen), skin (type I and type III collagens), tendon (type I collagen), cartilage (type II collagen), and ligament (type I collagen). Therefore, a large quantity of fiber-forming collagen-rich tissues can be harvested from the abattoirs. Since fiber-forming collagens are the major components of all extracellular matrices, it would be logical to use these collagens as the major ink component in bioprinting research and applications. The application of collagen-based ink materials for 3D bioprinting is intended to better control the material distribution within the ECM scaffolds or tissue equivalents to mimic the ECM or the tissue structure in vivo for enhancing tissue regeneration.

The current application of collagen for bioprinting is almost exclusively limited to soluble type I collagen molecules. They are extracted from enzyme pepsin digestion of insoluble collagen fibers to cleave the intermolecular cross-links, rendering the collagen soluble in dilute acidic conditions. However, the unique physicochemical properties of collagen solution have precluded the development of a suitable collagen-based ink for many bioprinting applications. As an example, collagen molecules are soluble in acidic solutions at less than 1% (10 mg/ml) (w/v) level, a concentration too low for practical printing purposes. They precipitate near neutral pH (the isoelectric point of the native collagen) or at body temperature to form fibers, which prevents the flow of collagen through the nozzle of the printer. Further, they denature at about 38° C., forming random coils, and lose all the characteristics of native collagen structure and biological properties and functions of the collagen in vivo. Thus, either the pH or the temperature can severely affect the printability of the collagen-based materials, let alone the low solubility of the collagen molecules.

Thus far, the majority of studies using collagen on 3D bioprinting limit the collagen concentration to the range of 0.5% to 1% (5 to 10 mg/ml) collagen solutions and rely on the control of its gelation properties (hydrogel formation) with temperature and pH control, or use supportive hydrogel (e.g., gelatin slurry), which acts as temporary thermo-reversible support technique (Hinton, T J et al., 2015, Sci Adv, 1: e1500758.). In any event, the collagen concentration in the bioink is very low due to its limited solubility properties.

Therefore, there is a critical need in the field of bioprinting to develop a collagen-based ink for 3D bioprinting to simulate the tissue and organ structures in the body.

SUMMARY OF THE INVENTION

This disclosure addresses the need mentioned above in a number of aspects. In one aspect, this disclosure provides a collagen fiber-based ink for bioprinting. In some embodiments, the collagen fiber-based ink comprises a dispersion of solid collagen fiber particles in an aqueous phase, wherein the collagen fiber particles are at a concentration greater than 1% (w/v), and wherein the collagen fiber particles have from about 240 moles of negative charges/mole collagen to about 240 moles positive charges/mole collagen.

In some embodiments, the collagen fiber particles have a substantially zero net electrical charge.

In some embodiments, the concentration of the collagen fiber particles is from about 2% (w/v) to about 25% (w/v). In some embodiments, the concentration of the collagen fiber particles is from about 9% (w/v) to about 23% (w/v).

In some embodiments, the collagen fiber particles have an average particle size of from about 10 μm to about 150 μm.

In some embodiments, the collagen fiber-based ink has a pH that is within about 1 pH unit below or above isoelectric point (pI) of the collagen fiber particles. In some embodiments, the pH is the isoelectric point of the collagen fiber particles. In some embodiments, the pH is from about 4.7 to about 7.2. In some embodiments, the pH is about 4.8.

In some embodiments, the collagen fiber-based ink is adapted to print a 3D structure using a nozzle having a diameter of from about 0.4 mm to about 2 mm.

In some embodiments, the 3D structure or the collagen fiber-based ink comprises an extracellular matrix (ECM).

In some embodiments, the aqueous phase comprises water or a saline solution. In some embodiments, the aqueous phase comprises an acetate buffer or a phosphate buffer.

In some embodiments, the collagen fiber particles are not enzyme-treated or acid-treated. In some embodiments, the collagen fiber particles do not contain atelocollagen or soluble intact collagen with telopeptides. In some embodiments, the collagen fiber particles comprise type I collagen, type II collagen, type III collagen, genetically engineered equivalents thereof, or a combination thereof. In some embodiments, the collagen fiber particles comprise type I collagen. In some embodiments, the collagen fiber particles comprise type II collagen.

In some embodiments, the collagen fiber-based ink comprises a cell. In some embodiments, the cell comprises a differentiated tissue specific cell. In some embodiments, the cell comprises an undifferentiated stem cell.

In some embodiments, the collagen fiber-based ink comprises a macromolecule. In some embodiments, the macromolecule comprises a growth factor, a cytokine, alginate, cellulose, agarose, chitosan, glycosaminoglycan, fibronectin, laminin, elastin, fibrin, gelatin, gelatin methacryloyl, collagen methacryloyl, a synthetic polymer, or a combination thereof.

In some embodiments, the collagen fiber-based ink comprises a mineral. In some embodiments, the mineral comprises hydroxyapatite, carbonate apatite, tricalcium phosphate, calcium sulfate, or a combination thereof.

In some embodiments, the collagen fiber-based ink comprises a decellularized collagen-rich tissue. In some embodiments, the decellularized collagen-rich tissue is derived from skin, bone, cartilage, tendon, ligament, muscle, nerve, liver, or blood vessel.

In another aspect, this disclosure also provides a kit comprising the collagen fiber-based ink described herein.

In another aspect, this disclosure further provides a method of preparing the collagen fiber-based ink. The method comprises: (a) obtaining purified collagen fibers from a collagen-rich tissue; (b) comminuting (e.g., cryo-milling) the purified collagen fiber into collagen fiber particles having an average particle size of from about 10 μm to about 150 μm; and (c) hydrating the collagen fiber particles with a solution to form an extrudable collagen fiber-based ink.

In some embodiments, the solution comprises an acetate buffer or a phosphate buffer. In some embodiments, the solution comprises gelatin methacryloyl.

In some embodiments, step (a) further comprises: removing immunogenic materials from the collagen-rich tissue by applying acid, base, alcohol, detergent, enzyme, and water to render the collagen-rich tissue biocompatible and implantable.

In some embodiments, step (c) comprises hydrating the collagen fiber particles with the solution having a pH that is within about 1 pH unit below or above the isoelectric point of the collagen fiber particles.

In some embodiments, prior to step (c), the method comprises dissolving gelatin methacryloyl in the solution.

In another aspect, this disclosure additional provides a collagen fiber-based ink prepared by the method described herein.

In another aspect, this disclosure also provides a method of printing a 3D structure. In some embodiments, the method comprises extruding the collagen fiber-based ink described herein with a bioprinter or a 3D printer.

In yet another aspect, this disclosure provides a method of printing a 3D structure. In some embodiments, the method comprises: (a) obtaining purified collagen fibers from a collagen-rich tissue; (b) comminuting (e.g., cryo-milling) the purified collagen fiber into collagen fiber particles having an average particle size of from about 10 μm to about 150 μm; (c) hydrating the collagen fiber particles with a solution to form an extrudable collagen fiber-based ink; and (d) extruding the collagen fiber-based ink with a bioprinter or a 3D printer to print the 3D structure.

In some embodiments, step (c) comprises hydrating the collagen fiber particles with the solution having a pH that is within about 1 pH unit below or above the isoelectric point of the collagen fiber particles.

In some embodiments, the 3D printer is an inkjet printer, a robotic dispensing printer, a mechanical extrusion printer, or a laser-based printer. In some embodiments, the bioprinter or 3D printer comprises a nozzle having a diameter of from about 0.4 mm to about 2 mm.

In some embodiments, the 3D structure comprises an ECM. In some embodiments, the ECM formed immediately after printing has a solid content substantially identical to native tissue.

In yet another aspect, this disclosure further provides a 3D structure formed according to the method described herein.

In some embodiments, the collagen fiber particles do not contain atelocollagen or soluble intact collagen with telopeptides. In some embodiments, the collagen fiber particles comprise type I collagen, type II collagen, type III collagen, genetically engineered equivalents thereof, or a combination thereof.

In some embodiments, the 3D structure comprises collagen fiber particles at a concentration of from about 2% (w/v) to about 25% (w/v). In some embodiments, the concentration of the collagen fiber particles is from about 9% (w/v) to about 23% (w/v).

In some embodiments, the collagen fiber particles have an average particle size of from about 10 μm to about 150 μm.

In some embodiments, the collagen fiber-based ink has a pH that is within about 1 pH unit below or above isoelectric point of the collagen fiber particles.

In some embodiments, the 3D structure comprises an ECM.

In some embodiments, the 3D structure further comprises an additional component. In some embodiments, the additional component comprises a cell, a macromolecule, a mineral, a decellularized collagen-rich tissue, or a combination thereof.

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the invention will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

DETAILED DESCRIPTION OF THE INVENTION

Figure 1:
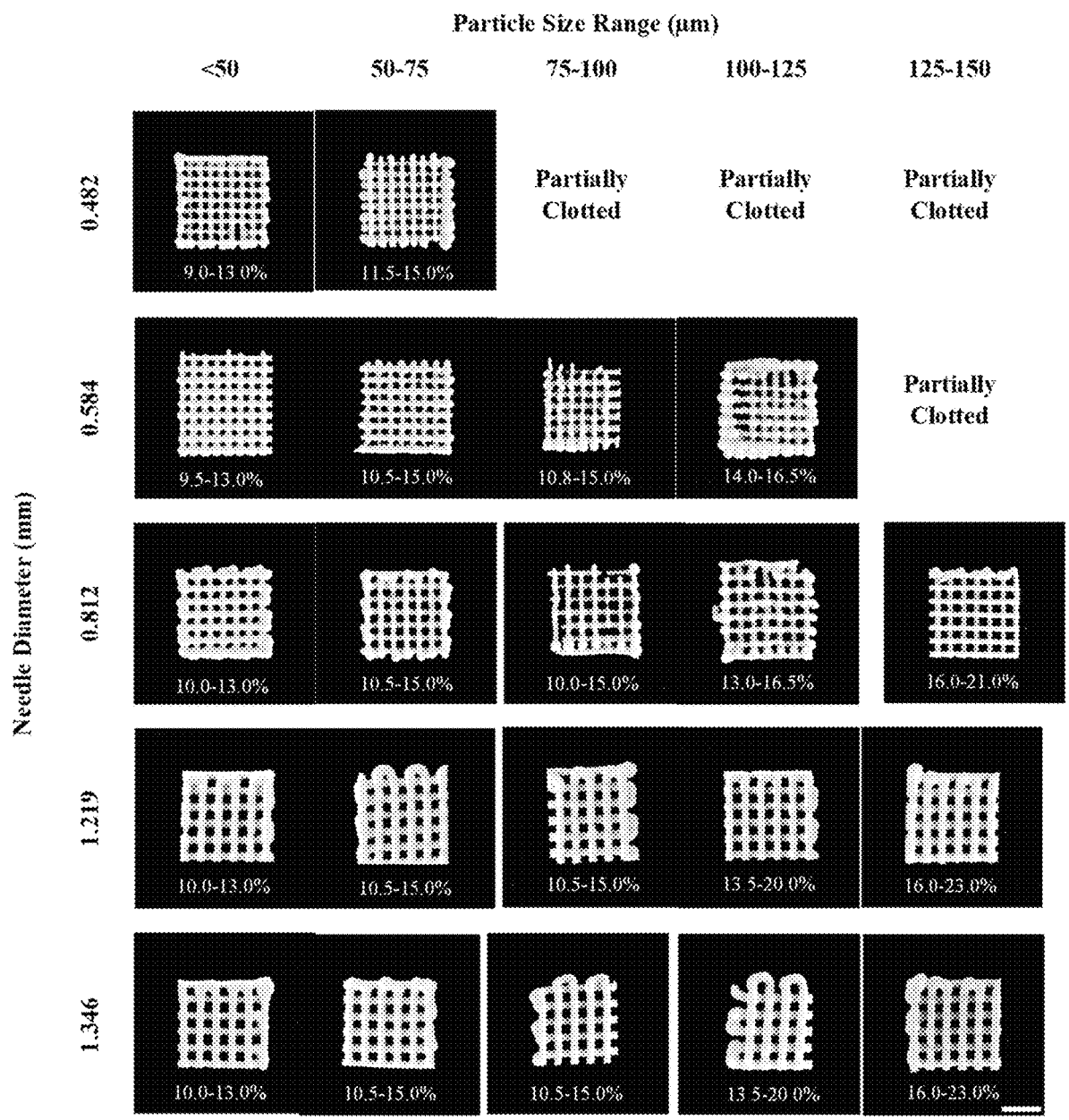
FIG. 1 shows the results of bioprinting of type I collagen fiber-based scaffolds under various conditions at pH 4.8 at room temperature. All photos were taken at the same magnification. Scale bar indicates 5 mm.

To date, the science and technology of regenerative medicine have advanced to the level that 3D bioprinting has become an important tool for tissue engineering research and development. By applying bioprinting, various bioactive components can be engineered into a 3D extracellular matrix (ECM) scaffold and tissue equivalent implant mimicking the native structures to perform their spatial and temporal functions in vivo.

Collagen Fiber-Based Ink

This disclosure provides a collagen fiber-based ink for bioprinting that comprises a surprisingly high solid content of collagen fiber particles (e.g., greater than 1% (w/v)). In one aspect, this disclosure provides a biocompatible and bioresorbable collagen fiber-based ink with a density of collagen equivalent to the density of collagen in native tissues. In another aspect, this disclosure also provides a collagen fiber-based ink for manufacturing collagen-based scaffolds and tissue equivalent implants for regenerative medicine applications.

In some embodiments, the collagen fiber-based ink comprises a dispersion of solid collagen fiber particles in an aqueous phase. In some embodiments, the collagen fiber-based ink comprises a dispersion of solid collagen fiber particles in an aqueous phase, wherein the collagen fiber particles are at a concentration greater than 1% (w/v). In some embodiments, the collagen fiber particles have from about 240 moles of negative charges/mole collagen to about 240 moles positive charges/mole collagen.

In some embodiments, the collagen fiber particles have a substantially zero net electrical charge.

The term "dispersion" refers to a disperse system in which one substance, the dispersed phase (e.g., collagen fiber particles) is distributed in discrete units throughout a second substance (the continuous phase or vehicle). The size of the dispersed phase can vary (e.g., microns in size).

The term "ink" or "bioink," as used herein, refers to a cell compatible material that can be used for bioprinting, e.g., by subjecting it to extrusion. Bioinks may be extruded through a needle between 0-37° C. and then can be gelled or solidified. They can be formulated for inkjet, laser-assisted, or microvalve 3D printing equipment.

This disclosure is based, at least in part, on the unexpected discovery that at the isoelectric pH, collagen microfibers are in the compact geometry, which permits a high collagen content to be printed. Under this condition, collagen content up to 25% (w/v) or higher can be printed into 3D structures (see FIGS. 1 and 2). In contrast to the existing collagen solution inks, the disclosed collagen fiber-based ink comprises collagen microfibers in a buffer solution at the pH of the isoelectric point of the collagen, generally from pH 4.7 to pH 7 depending on the purification process of the collagen.

As demonstrated in this disclosure, the density of the collagen in the ink can be controlled by adjusting the pH of the solution. At higher or lower pH away from the isoelectric point, the microfibers swell. Depending on the extent of pH shifts from the isoelectric point of the collagen, various collagen content per unit volume can be obtained, i.e., various pore sizes and pore volumes of the scaffolds can be controlled and printed. Thus, regional control of the pore structure of a scaffold can be mapped out by 3D bioprinting techniques.

By way of the density and pore structure control, other physical properties such as mechanical properties, cell density and distribution, and macromolecular density and distribution can all be designed into the engineered scaffolds and tissue equivalent implants. This can be accomplished by using multichannel nozzles with different combinations of collagen, cells, and macromolecules to print the desired 3D structure in different regions of a scaffold or tissue equivalent implant.

In some embodiments, the collagen fiber-based ink has a pH that is within about 1 pH unit below or above the isoelectric point of the collagen fiber particles. In some embodiments, the pH is the isoelectric point of the collagen fiber particles. In some embodiments, the pH is from about 4.7 to about 7.2 (e.g., pH 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2). In some embodiments, the pH is about 4.8.

In some embodiments, the collagen fiber particles are at a concentration greater than 1% (w/v). In some embodiments, the concentration of the collagen fiber particles is from about 2% (w/v) to about 25% (w/v), e.g., 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight of the collagen fiber-based ink. In some embodiments, the concentration of the collagen fiber particles is from about 9% (w/v) to about 23% (w/v).

In some embodiments, the concentration of the collagen fiber particles is from about 20 mg/ml to about 250 mg/ml, e.g., 20 mg/ml, 30 mg/ml, 40 mg/ml, 50 mg/ml, 60 mg/ml, 70 mg/ml, 80 mg/ml, 90 mg/ml, 100 mg/ml, 110 mg/ml, 120 mg/ml, 130 mg/ml, 140 mg/ml, 150 mg/ml, 160 mg/ml, 170 mg/ml, 180 mg/ml, 190 mg/ml, 200 mg/ml, 210 mg/ml, 220 mg/ml, 230 mg/ml, 240 mg/ml, 240 mg/ml, or 250 mg/ml. In some embodiments, the concentration of the collagen fiber particles is from about 90 mg/ml to about 230 mg/ml.

In some embodiments, the collagen fiber particles have an average particle size of from about 10 μm to about 150 μm (e.g., 10 μm, 15 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 100 μm, 105 μm, 110 μm, 115 μm, 120 μm, 125 μm, 130 μm, 135 μm, 140 μm, 145 μm, 150 μm).

In some embodiments, at least about 10%, 20%, 30%, 40%, 50%, 60%, 70%, 80% or 90% of collagen fiber particles can be about 10 μm to about 150 μm in its largest dimension (e.g., length), e.g., about 25 μm to about 150 μm, about 25 μm to about 125 μm, about 25 μm to about 100 μm, or about 25 μm to about 75 μm in its largest dimension. In some embodiments, the collagen fiber particles may have the largest dimension of less than about 150 μm. In some embodiments, the collagen fiber particles have the largest dimension of less than about 125 µm. In some embodiments, the r collagen fiber particles have the largest dimension of less than about 100 µm. In some embodiments, the collagen fiber particles have the largest dimension of less than about 75 µm. In some embodiments, the collagen fiber particles have the largest dimension of less than about 50 µm.

In some embodiments, the collagen fiber particles can have an average length of between about 10 µm to about 150 µm (e.g., 10 µm, 15 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm, 100 µm, 105 µm, 110 µm, 115 µm, 120 µm, 125 µm, 130 µm, 135 µm, 140 µm, 145 µm, 150 µm). In some embodiments, the collagen fiber particles can have an average length of between about 10 µm to about 125 µm. In some embodiments, the collagen fiber particles can have an average length of between about 10 µm to about 100 µm. In some embodiments, the collagen fiber particles can have an average length of between about 10 µm to about 75 µm. In some embodiments, the collagen fiber particles can have an average length of between about 10 µm to about 50 µm. In some embodiments, the collagen fiber particles can have an average length of between about 25 µm to about 150 µm. In some embodiments, the collagen fiber particles can have an average length of between about 25 µm to about 125 µm. In some embodiments, the collagen fiber particles can have an average length of between about 25 µm to about 100 µm. In some embodiments, the collagen fiber particles can have an average length of between about 25 µm to about 75 µm. In some embodiments, the collagen fiber particles can have an average length of between about 25 µm to about 50 µm.

In some embodiments, the collagen fiber-based ink is adapted to print a 3D structure using a nozzle having a diameter of from about 0.4 mm to about 2 mm (e.g., 0.482 mm, 0.584 mm, 0.812 mm, 1.219 mm, 1.346 mm). In some embodiments, the collagen fiber-based ink is adapted to print a 3D structure using a nozzle having a diameter of about 0.584 mm.

In some embodiments, the 3D structure or the collagen fiber-based ink comprises an ECM. As used herein, the terms "extracellular matrix" and "ECM" refer to natural scaffolds for cell growth prepared by decellularizing tissues found in multicellular organisms (e.g., mammals and humans). The ECM can be further processed by, for example, dialysis or crosslinking. ECM is a complex mixture of structural and non-structural biomolecules, including but not limited to: collagen, elastin, fibronectin, aminopolysaccharide, proteoglycan, antibacterial agent, chemotactic cell-inducing factor, cytokine and/or growth factor. In mammals, the ECM often includes about 90% collagen in its various forms. The structure of ECM varies depending on the tissue source. For example, Small Intestinal Submucosa (SIS), bladder matrix (UBM), and liver matrix ECM differ in their overall structure due to the unique cellular environment required for each tissue. The terms "intact extracellular matrix" and "intact ECM" refer to an extracellular matrix whose structural or non-structural biomolecules remain active, including, but not limited to, collagen, elastin, fibronectin, glycosaminoglycans, proteoglycans, antimicrobials, chemotactic cell-inducing factors, cytokines, and/or growth factors, such as, but not limited to, comminuted ECM as described herein. Biomolecules in the ECM can be inactivated chemically or mechanically, for example, by crosslinking and/or by dialysis of the ECM. Intact ECM is substantially not crosslinked or dialyzed, which means that the ECM has not undergone a process of dialysis and/or crosslinking, or, prior to solubilization, has not undergone other than a process that naturally occurs when storing and processing the ECM, as described herein. Thus, an essentially crosslinked and/or dialyzed ECM is not considered "intact" in any way other than in those minor alterations that do not substantially affect the gelling and functional characteristics of the ECM in the applications described herein.

Examples of ECM include those described, e.g., in U.S. Pat. Nos. 4,902,508, 4,956,178, 5,281,422, 5,352,463, 5,372,821, 5,554,389, 5,573,784, 5,645,860, 5,711,969, 5,753,267, 5,762,966, 5,866,414, 6,099,567, 6,485,723, 6,576,265, 6,579,538, 6,696,270, 6,783,776, 6,793,939, 6,849,273, 6,852,339, 6,861,074, 6,887,495, 6,890,562, 6,890,563, 6,890,564, and 6,893,666, the disclosures of which are herein incorporated by reference in their entirety. In some embodiments, the ECM is derived from a vertebrate, such as, but not limited to, a mammalian vertebrate derived from warmblood, including, but not limited to, humans, monkeys, pigs, cows, and sheep. The ECM may be derived from any organ or tissue, including, but not limited to, bladder, intestine, liver, esophagus, and skin. In one embodiment, the ECM is isolated from the bladder. In another embodiment, the ECM is isolated from the intestine or a portion thereof. The intestine extends from the pyloric sphincter to the anus, and includes a small intestine extending from the pyloric valve to the ileocaecal valve; the large intestine, which extends from the ileocaecal valve; and other parts, including the duodenum; jejunum; the ileum; the cecum; an accessory; ascending colon, transverse colon, descending colon, and sigmoid colon; the rectum and/or anal canal (see, e.g., Marieb, EN, Human Anatomy and Physiology; second edition, 1992, Benjamin/Cummings printing limited, Redwood city, ca, pages 792,793,802, and 803). In some embodiments, the ECM comprises at least a portion of the basement membrane.

In some embodiments, the aqueous phase comprises water or a saline solution (e.g., sodium chloride solution). The saline solution can be buffered or unbuffered solution. In some embodiments, the aqueous phase comprises an acetate or a citrate buffer (e.g., sodium acetate standard buffer or sodium citrate buffer having pH 4.0 to 6.2); a phosphate buffer (e.g., sodium phosphate buffer or potassium phosphate buffer having pH 5.8 to 7.4); or a Tris buffer having pH 7.0 to 7.5.

The term "collagen," as used herein, refers to a natural protein having the molecular structure known as atelocollagen, telocollagen, tropocollagen, procollagen, polymeric collagen, fibrillar collagen, electrospun collagen, insoluble collagen, soluble collagen, precipitated collagen, or collagen dough. "Native collagen" refers to collagen that retains normal conformation, unlike gelatin that is collagen that has been irreversibly hydrolyzed.

In some embodiments, the collagen fiber particles are not enzyme-treated or acid-treated. In some embodiments, the collagen fiber particles do not contain atelocollagen or soluble intact collagen with telopeptides (also referred to as protocollagen). In some embodiments, the collagen fiber particles comprise type I collagen, type II collagen, type III collagen, genetically engineered equivalents thereof, or a combination thereof. In some embodiments, the collagen fiber particles comprise type I collagen. In some embodiments, the collagen fiber particles comprise type II collagen.

In some embodiments, the collagen fiber-based ink comprises a cell. In some embodiments, the cell comprises a differentiated tissue specific cell. In some embodiments, the cell comprises an undifferentiated stem cell.

As used herein, the term "cell" or "cell population" is meant to be any kind of cell from any animal, such as, but not limited to, rat, mouse, monkey, and human. For example, but not limited to, the cells may be progenitor cells, such as stem cells, or differentiated cells, such as endothelial cells, and smooth muscle cells. In some embodiments, the cells used for the medical procedure may be from a patient, used in an autologous procedure, or derived from another donor, suitable for a heterologous procedure.

In some embodiments, the collagen fiber-based ink comprises a macromolecule. In some embodiments, the macromolecule comprises a growth factor, a cytokine, alginate, cellulose, agarose, chitosan, glycosaminoglycan, fibronectin, laminin, elastin, fibrin, gelatin, gelatin methacryloyl, collagen methacryloyl, a synthetic polymer, or a combination thereof.

In some embodiments, the collagen fiber-based ink comprises a mineral. In some embodiments, the mineral comprises hydroxyapatite, carbonate apatite, tricalcium phosphate, calcium sulfate, or a combination thereof.

In some embodiments, the collagen fiber-based ink comprises a decellularized collagen-rich tissue. In some embodiments, the decellularized collagen-rich tissue is derived from skin, bone, cartilage, tendon, ligament, muscle, nerve, liver, or blood vessel.

In some embodiments, the collagen fiber-based ink described herein can be provided in a kit. In one embodiment, the kit includes (a) a container that contains the collagen fiber-based ink, and optionally (b) informational material. The informational material can be descriptive, instructional, marketing or other material that relates to the methods described herein and/or the use of the collagen fiber-based ink. In an embodiment, the kit includes also includes an additional agent. For example, the kit includes a first container that contains the collagen fiber-based ink and a second container for the additional agent. In some embodiments, the additional agent comprises a cell, a macromolecule, a mineral, a decellularized collagen-rich tissue, or a combination thereof.

The informational material of the kits is not limited in its form. In one embodiment, the informational material can include information about production of the collagen fiber-based ink, concentration, date of expiration, batch or production site information, and so forth. In one embodiment, the informational material relates to methods of using the disclosed collagen fiber-based ink to print a 3D structure. In some embodiments, the information can be provided in a variety of formats, including printed text, computer-readable material, video recording, or audio recording, or information that contains a link or address to substantive material.

In addition to the ink, the kit can include other ingredients, such as a solvent or buffer, a stabilizer, or a preservative. The collagen fiber-based ink can be provided in any form, e.g., liquid, dried or lyophilized form, preferably substantially pure and/or sterile. When the collagen fiber-based ink is provided in a liquid phase, the liquid solution preferably is an aqueous solution. When the collagen fiber-based ink is provided as a dried form, reconstitution generally is by the addition of a suitable solvent and acidulant. The acidulant and solvent, e.g., an aprotic solvent, sterile water, or a buffer, can optionally be provided in the kit.

The kit optionally includes a device suitable for loading the collagen fiber-based ink, e.g., to a 3D printer, such as a syringe or other suitable delivery device. The device can be provided pre-loaded with one or both of the agents or can be empty, but suitable for loading.

Methods of Preparing Collagen Fiber-Based Ink

In another aspect, this disclosure further provides a method of preparing the collagen fiber-based ink. The method comprises: (a) obtaining purified collagen fibers from a collagen-rich tissue; (b) comminuting (e.g., cryomilling) the purified collagen fiber into collagen fiber particles having an average particle size of from about 10 μm to about 150 μm; and (c) hydrating the collagen fiber particles with a solution to form an extrudable collagen fiber-based ink.

In some embodiments, the solution comprises an acetate buffer or a phosphate buffer. In some embodiments, the solution comprises gelatin methacryloyl.

In some embodiments, step (a) further comprises: removing immunogenic materials from the collagen-rich tissue by applying acid, base, alcohol, detergent, enzyme, and water to render the collagen-rich tissue biocompatible and implantable. In some embodiments, prior to step (c), the method comprises dissolving gelatin methacryloyl in the solution.

The term "comminution," as used herein, refers to a process of processing large particles into small particles, including, but not limited to, grinding, milling, blending, shredding, cutting, crushing, cutting, shredding, and the like.

In some embodiments, step (b) comprises cryo-milling the purified collagen fiber into collagen fiber particles having an average particle size of from about 10 μm to about 150 μm.

In some embodiments, step (c) comprises hydrating the collagen fiber particles with the solution having a pH that is within about 1 pH unit below or above the isoelectric point of the collagen fiber particles. In some embodiments, the pH is the isoelectric point of the collagen fiber particles. In some embodiments, the pH is from about 4.7 to about 7.2 (e.g., pH 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2). In some embodiments, the pH is about 4.8.

The term "biocompatible," as used herein, refers to a device, scaffold, 3D structure, etc., is substantially non-toxic, harmless, or non-inhibitory to the cell, tissue, organ and/or organ system with which it is in contact, actually (for its intended use), and/or substantially.

The preparation of an example type I collagen microfiber bioink is demonstrated in Example 1. Type II collagen-based microfiber bioink can be prepared from type II collagen rich tissues such as articular cartilage from the joints of bovine or porcine and from sternum of chicken. The preparation of an example type II collagen fiber bioink is demonstrated in Example 5.

In addition to the purified individual components that can be incorporated into an ink such as that described in Examples 2-4, natural tissue specific decellularized matrices (dECM) can be developed by a mild process to remove the cell components, including cell debris, DNA, RNAs, and other potential immunogenic materials (e.g., agalactose-related epitopes) from the tissues such that dECM bioinks close to the intact tissue specific ECM scaffold can be developed.

The decellularization processes for various tissues are described in, e.g., Folguli Pati and Dong-Woo Cho, 2017, Methods Mol. Biol. 1612:381-390; Andrea J. Vernengo, et al., Adv. Functional Materials, 30:1909044, 2021; Alperen Abaci and Murate Guvendiren, A Biofabrication, 10.1088/1758-5090/ac4fb6, 14, 2 (025013) (2022), the disclosures of which are herein incorporated by reference in their entirety. The resulting decellularized matrices have structures that more closely mimic the intact tissues or organs at the microscopic level for information transduction at the cellular and molecular level. By using the disclosed methods, high density collagen fiber-based dECM ink can contain up to 25% of various types of collagens (w/v) can be developed. Preparation of example dECM-based microfiber inks is demonstrated in Example 6.

Methods of preparing ECM require the isolation of the ECM from the animal body of interest or an organ of interest. In some embodiments, the ECM is isolated from mammalian tissue. As used herein, the term "mammalian tissue" refers to tissue derived from a mammal, wherein the tissue includes any cellular component of an animal. For example, but not limited to, the tissue may be derived from a collection of cells, e.g., an organ, organ portion, or organ combination. In certain embodiments, the ECM is derived from a vertebrate, such as, but not limited to, a human, a monkey, a pig, a cow, and a sheep. In certain embodiments, the ECM is derived from any tissue of an animal, such as, but not limited to bladder, liver, Central Nervous System (CNS), adipose tissue, small intestine, large intestine, colon, esophagus, pancreas, dermis, and heart. In one embodiment, the ECM is from the bladder. The ECM may or may not include a basement membrane portion of the ECM. In certain embodiments, the ECM comprises at least a portion of the basement membrane. The ECM may or may not retain some cellular molecules, including the original tissue, such as capillary endothelial cells or fibroblasts. As used herein, the term "derived from" refers to a component or components obtained by any effective method from any of the sources. ECM can be obtained from any tissue by using various methods known in the art suitable for isolating ECM.

After isolation of the tissue of interest, decellularization is performed by various methods, such as, but not limited to, exposure to hypertonic saline, peracetic acid, Triton-X, or other detergents. The decellularized ECM is then dried or freeze-dried (lyophilized) or air-dried. The dried ECM may be comminuted by a number of methods, including, but not limited to, tearing, crushing, cutting, grinding, and shearing. The comminuted ECM may also be further processed into a powder by methods including, but not limited to, grinding or crushing the ECM in a frozen or freeze-dried state, for example. The ECM may be comminuted, although not limited to any form, including, but not limited to, hydrated, frozen, air-dried, freeze-dried, powder, or flake. In some embodiments, to prepare solubilized ECM tissue, the comminuted ECM can be digested with an acidic protease in an acidic solution to form a digestion solution. As used herein, the term "acid protease" refers to an enzyme capable of cleaving peptide bonds, wherein the enzyme may increase the ability to cleave peptide bonds at acidic pH values. For example, but not limited to, acidic proteases may include pepsin and trypsin.

In some embodiments, an ECM can be prepared from isolated collagen at collagen concentrations ranging from about 0.05 to about 5.0 mg/ml, about 1.0 mg/ml to about 3.0 mg/ml, about 0.05 mg/ml to about 10 mg/ml, about 0.05 to about 20 mg/ml, about 0.05 to about 30 mg/ml, about 0.05 to about 40 mg/ml, about 0.05 to about 50 mg/ml, about 0.05 to about 60 mg/ml, about 0.05 to about 80 mg/ml, about 5 mg/ml to 10 mg/ml, about 5 mg/ml to 20 mg/ml, about 5 mg/ml to about 40 mg/ml, about 5 mg/ml to 60 mg/ml, about 5 mg/ml to about 100 mg/ml, about 20 mg/ml to about 40 mg/ml, about 20 mg/ml to 60 mg/ml, about 20 mg/ml to about 100 mg/ml, or about 20 mg/ml to about 120 mg/ml, about 20 mg/ml to about 140 mg/ml, about 20 mg/ml to about 160 mg/ml, about 20 mg/ml to about 180 mg/ml, about 20 mg/ml to about 180 mg/ml, about 20 mg/ml to about 180 mg/ml, about 20 mg/ml to about 200 mg/ml, about 20 mg/ml to about 220 mg/ml, about 20 mg/ml to about 240 mg/ml, about 20 mg/ml to about 250 mg/ml.

In another aspect, this disclosure additional provides a collagen fiber-based ink prepared by the method described herein.

Methods of Printing a 3D Structure

In another aspect, this disclosure also provides a method of printing a 3D structure. In some embodiments, the method comprises extruding the collagen fiber-based ink described herein with a bioprinter or a 3D printer.

In yet another aspect, this disclosure provides a method of printing a 3D structure. In some embodiments, the method comprises: (a) obtaining purified collagen fibers from a collagen-rich tissue; (b) comminuting the purified collagen fiber into collagen fiber particles having an average particle size of from about 10 µm to about 150 µm; (c) hydrating the collagen fiber particles with a solution to form an extrudable collagen fiber-based ink; and (d) extruding the collagen fiber-based ink with a bioprinter or a 3D printer to print the 3D structure. The printed 3D structure then can be dried using any suitable methods (e.g., freeze-drying) to remove the water without altering the size or shape of the structure. Optionally, a subsequent crosslinking step (e.g., chemical crosslinking) can be applied to stabilize the structure.

In some embodiments, step (b) comprises cryo-milling the purified collagen fiber into collagen fiber particles having an average particle size of from about 10 µm to about 150 µm.

In some embodiments, step (c) comprises hydrating the collagen fiber particles with the solution having a pH that is within about 1 pH unit below or above the isoelectric point of the collagen fiber particles. In some embodiments, the pH is the isoelectric point of the collagen fiber particles. In some embodiments, the pH is from about 4.7 to about 7.2 (e.g., pH 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2). In some embodiments, the pH is about 4.8.

In some embodiments, the 3D structure comprises an ECM. One of the advantages of the disclosed collagen fiber-based ink is that the ECM formed immediately after printing has a solid content substantially identical to native tissue. The term "ECM formed immediately after printing," as used herein, refers to an ECM formed by extruding the disclosed collagen fiber-based ink without further treatment, such as drying, crosslinking, coating, stabilization, and the link.

In some embodiments, the method is a computer implemented method. The method may comprise instructing a 3D printer coupled to a computer to generate the 3D structure based on a pre-determined 3D digital model.

In some embodiments, the 3D printer is an inkjet printer, a robotic dispensing printer, a mechanical extrusion printer, or a laser-based printer. In some embodiments, the bioprinter or 3D printer comprises a nozzle having a diameter of from about 0.4 mm to about 2 mm.

Inkjet printing is a non-contact strategy based on the deposition of bioink drops in a predesigned manner to form a final multilayer pattern. Robotic dispensing printing can be continuous extrusion where the ink is dispensed by a pneumatic or mechanical force or microvalve-based droplet ejection, which is a technique between inkjet and standard extrusion techniques. Laser-based printing is based on the transfer of a bioink from a donor substrate to a receiving substrate controlled by laser beam pulses that target a precisely defined position.

In some embodiments, the method may comprise adding cells to the 3D structure as the 3D structure is being printed.

In some embodiments, the method may comprise adding cells to the 3D structure after the 3D structure is printed. In some embodiments, the method may comprise printing cells on the 3D structure during or after printing. For example, a 3D printer with two or more nozzles may alternately or in some other pattern print a layer of bioink and a layer of cells. In some embodiments, the cells are incubated with the 3D structure after the 3D structure is printed so that cells may migrate onto or into the structure.

To best mimic a cell's native environment with 3D bioprinting, multiple extruders are often employed. Each extruder can be filled with a different bioink and cell type, to allow the printing of multiple layers of tissues. The multi-head system can also be used to print a structural scaffold out of synthetic material with one head, and then fill it in with a native material with another extruder.

The bioink may be printed into a support media or bath. In some embodiments, the support media comprises nutrients for cells. In some embodiments, the support media provides temporary support to the 3D structure, e.g., until the structure gels or is crosslinked. The temporary support may be provided by a support agent in the media, such as, without limitation, a gelatin slurry, a slurry of hydrogel particles, or a slurry of hydrophilic particles.

In yet another aspect, this disclosure further provides a 3D structure formed according to the method described herein.

In some embodiments, the collagen fiber particles do not contain atelocollagen or soluble intact collagen with telopeptides. In some embodiments, the collagen fiber particles comprise type I collagen, type II collagen, type III collagen, genetically engineered equivalents thereof, or a combination thereof.

In some embodiments, the 3D structure comprises collagen fiber particles at a concentration of from about 1% (w/v) to about 25% (w/v) e.g., 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight of the 3D structure. In some embodiments, the concentration of the collagen fiber particles is from about 9% (w/v) to about 23% (w/v).

In some embodiments, the collagen fiber particles have an average particle size of from about 10 μm to about 150 μm (e.g., 10 μm, 15 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 100 μm, 105 μm, 110 μm, 115 μm, 120 μm, 125 μm, 130 μm, 135 μm, 140 μm, 145 μm, 150 μm).

In some embodiments, the collagen fiber-based ink has a pH that is within about 1 pH unit below or above the isoelectric point of the collagen fiber particles. In some embodiments, the pH is the isoelectric point of the collagen fiber particles. In some embodiments, the pH is from about 4.7 to about 7.2 (e.g., pH 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2). In some embodiments, the pH is about 4.8.

In some embodiments, the 3D structure comprises an ECM.

In some embodiments, the 3D structure further comprises an additional component. In some embodiments, the additional component comprises a cell, a macromolecule, a mineral, a decellularized collagen-rich tissue, or a combination thereof.

In some embodiments, the collagen fiber-based ink comprises a cell. In some embodiments, the cell comprises a differentiated tissue specific cell. In some embodiments, the cell comprises an undifferentiated stem cell.

In some embodiments, the collagen fiber-based ink comprises a macromolecule. In some embodiments, the macromolecule comprises a growth factor, a cytokine, alginate, cellulose, agarose, chitosan, glycosaminoglycan, fibronectin, laminin, elastin, fibrin, gelatin, gelatin methacryloyl, collagen methacryloyl, a synthetic polymer, or a combination thereof.

In some embodiments, the collagen fiber-based ink comprises a mineral. In some embodiments, the mineral comprises hydroxyapatite, carbonate apatite, tricalcium phosphate, calcium sulfate, or a combination thereof.

In some embodiments, the collagen fiber-based ink comprises a decellularized collagen-rich tissue. In some embodiments, the decellularized collagen-rich tissue is derived from skin, bone, cartilage, tendon, ligament, muscle, nerve, liver, or blood vessel.

The 3D structures described herein may be used, for example and without limitation, as injectable grafts (e.g., allografts, or autografts) for use in tissues in need of repair or augmentation (e.g., bone or soft tissue), and more typically, in need of repair of tissue defects resulting from trauma or disease. The 3D structures may also be used as a graft construct filler, including, but not limited to, a cast construct formed into a desired shape for use in surgical procedures to decorate or treat wounds.

The 3D structures can be implanted into a patient, human or animal body by a variety of methods. In one non-limiting embodiment, the 3D structure is injected into the patient at the desired site in the body in liquid form. As used herein, the terms "seeding," "planting," or "transplanting" refer to the addition, integration, dissemination, or diffusion of a defined volume of a cell suspension or a defined number of cells to a particular 3D structure. The 3D structure may be pre-seeded with cells and then injected, preferably using a large size, e.g., 16 gauge needle, to prevent the cells from being shredded. In another non-limiting embodiment, the 3D structure is gel-formed in a mold, and the gel-formed, molded product is transplanted to a suitable site in the patient. The products of the colloid-forming mold can be pre-seeded with cells, for example, cells of a patient.

In some embodiments, the 3D structure comprises a hybrid inorganic/ECM scaffold. As used herein, the term "hybrid inorganic/ECM scaffold" refers to an ECM coated on a biocompatible inorganic structure, such as, but not limited to, a metal, an inorganic calcium compound (e.g., calcium hydroxide, calcium phosphate or calcium carbonate), or a ceramic 3D structure. In one embodiment, the inorganic structures are coated with an ECM using 3D printing.

As used herein, the term "coating" and its synonyms such as "coating" and "encapsulation" refer to a process that involves covering an inorganic structure with an ECM or hybrid inorganic/ECM scaffold. For example, but not limited to, coating an inorganic structure with an ECM may include pouring, filling, layering, soaking, spraying, and the like.

In some embodiments, the 3D structure is coated on a biocompatible structural material, such as a metal, an inorganic calcium compound (e.g., calcium hydroxide, calcium phosphate, or calcium carbonate), or a ceramic 3D structure. Non-limiting examples of suitable metals are cobalt chromium alloys, stainless steel, titanium alloys, tantalum alloys, titanium-tantalum alloys, which may include non-metallic and metallic components such as molybdenum, tantalum, niobium, zirconium, iron, manganese, chromium, cobalt, nickel, aluminum, and lanthanum, including, but not limited to, various grades of CP Ti (commercially pure titanium) or Ti6Al4V (90% by weight Ti, 6% by weight aluminum, and 4% by weight vanadium), stainless steel 316, nitinol (nickel titanium alloy), titanium alloys plated with hydroxyapatite. Metals are effective due to their high strength, flexibility and biocompatibility. Metals can also be formed into a variety of complex shapes and many metals are able to withstand corrosion from the biological environment, reduce wear, and do not cause damage to the tissue. In one non-limiting embodiment, the metal is a femoral or acetabular component for hip repair. In another embodiment, the metal is fibers or other protrusions for permanent attachment to the prosthesis of the patient. Other 3D structures, including ceramics, calcium compounds, such as, but not limited to, calcium carbonate, may be preferred, such as, but not limited to, use in the repair or reshaping of bone or tooth structures. Combinations of metals, ceramics and/or other materials have also proven effective. For example, the metal femoral component of the hip replacement may include a ceramic ball and/or may include plastic coated on the surface of the ball as the acetabular component.

Metals and other suitable materials may be used in their various forms including, but not limited to, wires, flakes, beads, rods, and powders, including nanocrystalline powders. The surface of the 3D structure and metal or other material may also be modified to preserve biocompatibility, for example, by silane treatment to passivate the surface, coating with biocompatible plastics or ceramics, composite metal/ceramic materials. The materials and methods used herein are known in the art to which this invention pertains.

Definitions

To aid in understanding the detailed description of the agents and methods according to the disclosure, a few express definitions are provided to facilitate an unambiguous disclosure of the various aspects of the disclosure. Unless otherwise defined, all technical and scientific terms used herein have the same meaning as commonly understood by one of ordinary skill in the art to which this disclosure belongs.

As used herein, a "subject" refers to a human and a non-human animal. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental animal or animal suitable as a disease model.

As used herein, the term "in vitro" refers to events that occur in an artificial environment, e.g., in a test tube or reaction vessel, in cell culture, etc., rather than within a multicellular organism.

As used herein, the term "in vivo" refers to events that occur within a multicellular organism, such as a non-human animal.

It is noted here that, as used in this specification and the appended claims, the singular forms "a," "an," and "the" include plural reference unless the context clearly dictates otherwise.

The terms "including," "comprising," "containing," or "having" and variations thereof are meant to encompass the items listed thereafter and equivalents thereof as well as additional subject matter unless otherwise noted.

The phrases "in one embodiment," "in various embodiments," "in some embodiments," and the like are used repeatedly. Such phrases do not necessarily refer to the same embodiment, but they may unless the context dictates otherwise.

The terms "and/or" or "/" means any one of the items, any combination of the items, or all of the items with which this term is associated.

The word "substantially" does not exclude "completely," e.g., a composition which is "substantially free" from Y may be completely free from Y. Where necessary, the word "substantially" may be omitted from the definition of the invention.

As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Unless indicated otherwise herein, the term "about" is intended to include values, e.g., weight percents, proximate to the recited range that are equivalent in terms of the functionality of the individual ingredient, the composition, or the embodiment.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

As used herein, the term "each," when used in reference to a collection of items, is intended to identify an individual item in the collection but does not necessarily refer to every item in the collection. Exceptions can occur if explicit disclosure or context clearly dictates otherwise.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. When used in this document, the term "exemplary" is intended to mean "by way of example" and is not intended to indicate that a particular exemplary item is preferred or required.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise.

In cases in which a method comprises a combination of steps, each and every combination or sub-combination of the steps is encompassed within the scope of the disclosure, unless otherwise noted herein.

Each publication, patent application, patent, and other reference cited herein is incorporated by reference in its entirety to the extent that it is not inconsistent with the present disclosure. Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates, which may need to be independently confirmed.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Example 1. Methods of Preparing Type I Collagen Fiber-Based Inks

Preparation of Purified Type I Collagen Fibers

The method of preparing purified type I collagen fibers is described in, e.g., U.S. Pat. Nos. 5,263,984, 5,735,902, 6,042,610, 6,391,333 and Li, S. T. Biologic Biomaterials: Tissue-Derived Biomaterials (Collagen) 2013, the disclosures of which are herein incorporated in their entirety. Briefly, fresh deep flexor tendons of bovine were obtained from a local abattoir. The tendons were cleaned, washed, and mechanically disintegrated into thin slices. The tissue slices were then extracted in acid, base, salt, alcohol, limited enzyme treatment, and water to remove the non-collageneous moieties from the tissue to render the purified tendon type I collagen biocompatible and implantable. The resulting purified type I collagen fibers had an isoelectric point between pH 4.7 to pH 7.0, depending on the purification procedure. The purified type I collagen fibers were freeze-dried and stored at 4° C.

Preparation of Type I Collagen Fiber-Based Inks

Purified type I collagen fibers prepared from the above were dried in a desiccator or in a vacuum chamber for 24 hrs. The dried fibers were then cut into small pieces with a mechanical knife cutter. 5 g of the dry type I collagen fiber pieces were inserted into a polycarbonate sample vial (Spex Freezer/Mill) which contained a stainless-steel impactor and two end plugs. The sample vial was then slotted into the dual electromagnetic grinder chamber. The chamber was then immersed in the liquid nitrogen bath. The solidified collagen fibers were subjected to the electromagnetic force that impacted the collagen fibers via the steel impactor to reduce the fiber sizes into microscopic fibers without inducing thermal degradation. With control of time, generally 4-10 minutes, various fiber sizes between 10 μm to 150 μm were obtained.

The micro-fibers were then sieved to produce several fiber size groups, including fiber sizes <50 μm, 50-75 μm, 75-100 μm, 100-125 μm, and 125-150 μm. Fiber sizes of the above ranges were used for the preparation of collagen fiber-based inks at two buffer solutions, one at pH 4.8 (acetate buffer) and the other at pH 7.2 (phosphate buffer), to print 3D scaffolds using nozzle sizes of 0.482 mm, 0.584 mm, 0.812 mm, 1.219 mm and 1.346 mm. The general procedure for preparing type I collagen fiber-based inks (<50 μm) is described as follows.

Fixed weight of microfibers is placed into a 20 ml centrifuge tube with a graded volume scale for measuring the total volume occupied by the collagen microfibers and the solution. An excess amount of solution (e.g., 15 ml) of defined pH (e.g., acetate buffer at pH 4.8 or phosphate buffer at pH 7.2) was added and agitated (Nutating Mixture) for 2 to 4 hours to fully hydrate the microfibers. The hydrated fibers were then centrifuged (Universal 320 Centrifuge) at 3000 to 4500 RPM to form a hydrated, cohesive extrudable collagen microfiber ink. It typically takes 4-6 minutes to reach a constant volume of hydrated microfiber ink. Generally, at the isoelectric point, the fibers are at their compact conformation, higher collagen density ink will be formed. In terms of the effect of fiber size, the larger the fiber size, the higher density of the ink will form. Since collagen has a higher density than water, it appears that larger fibers of a given weight would occupy less volume than the smaller fibers of the same weight in a given volume.

Figure 2:
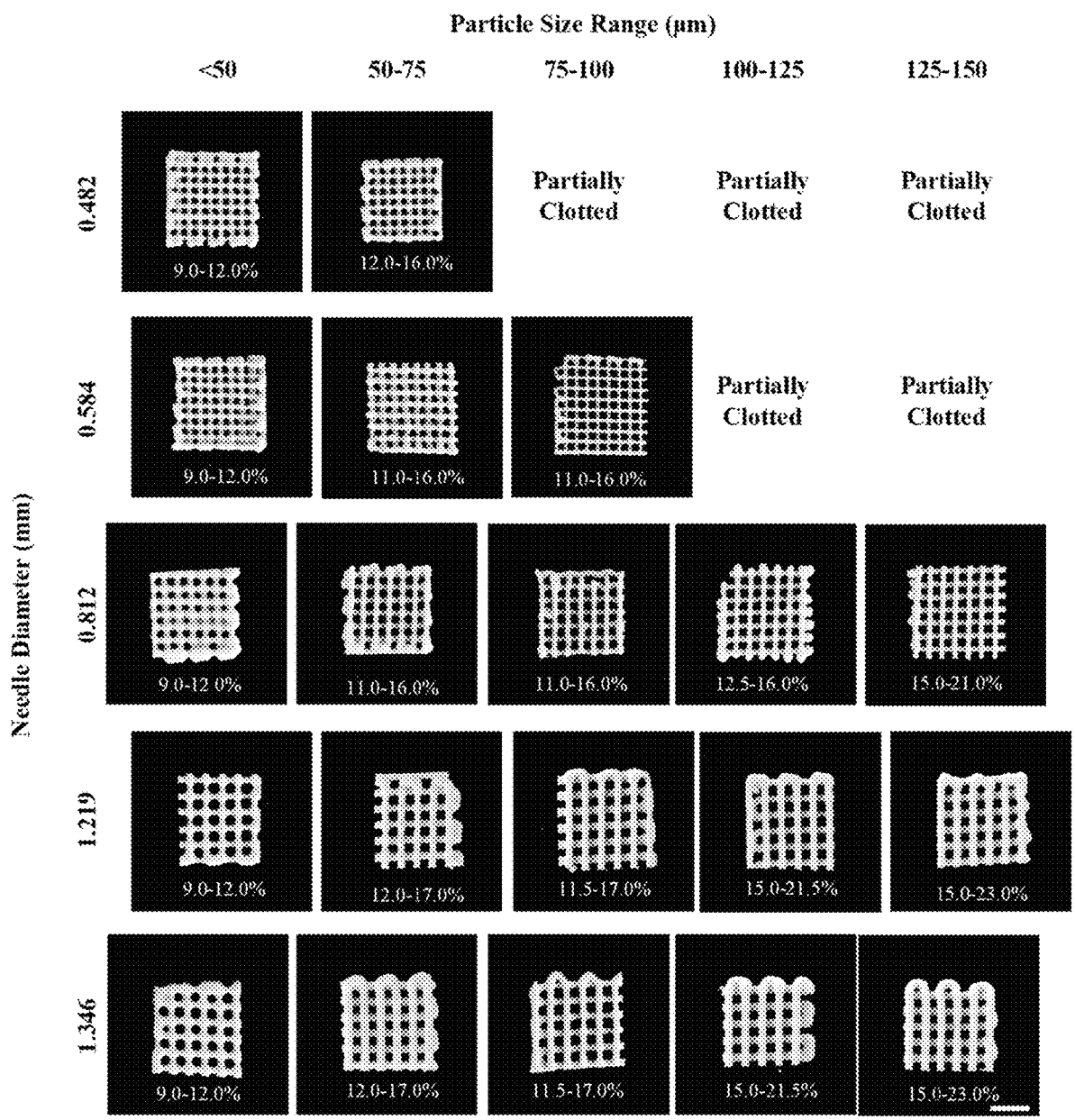
FIG. 2 shows the results of bioprinting of type I collagen fiber-based scaffolds under various conditions at pH 7.2 at room temperature. All photos were taken at the same magnification. Scale bar indicates 5 mm.

FIGS. 1 and 2 summarize the results of the inks prepared under various conditions. As demonstrated, the ink with a collagen content of from 9 to 23% can be readily prepared.

Method of Printing of Type I Collagen Fiber-Based Ink

A typical example of printing a type I collagen fiber-based ink at pH 4.8 is as follows. 1.4 g of type I collagen fibers (50-75 μm) was hydrated in 15-20 ml of a sodium acetate buffer at pH 4.8, the isoelectric point of this collagen. At this pH, the microfibers are in the most compact geometry. Upon hydration of the microfibers for several hours under agitation, the excess solution was removed via centrifugation (e.g., Universal 320 Centrifuge at 3,000 to 4500 RPM for 4-6 mins). The final volume was around 10 ml. Taking the density of collagen to be 1.41 g/ml, the volume occupied by collagen would be around 1 ml. Therefore, the solid collagen content in the hydrated ink was about 14% (w/v). The hydrated collagen had physical properties similar to toothpaste. The ink was extruded using a nozzle size of 0.584 mm (see FIG. 1)

Since the ink contained significant solid content, the printed 3D scaffolds can be removed from the printer housing for further processing without the need of performing any steps of scaffold stabilization, such as UV cross-linking by incorporating light-sensitive polymers into the ink (e.g., gelatin methacryloyl) as that commonly used for soluble collagen ink preparations. The printed scaffold was subsequently subjected to freeze-drying to remove the water without altering the size or shape of the scaffold. A subsequent chemical crosslinking post freeze-drying was applied to stabilize the scaffold and control the rate of in vivo resorption.

FIGS. 1 and 2 summarize the printed type I collagen fiber scaffolds under various printing conditions. FIG. 1 demonstrates the printability of the various fiber sizes of type I collagen fiber-based ink, the range of collagen fiber content (w/v) of the ink, and the suitability of the nozzle diameter for each collagen-fiber ink printed at pH 4.8 at room temperature. FIG. 2 demonstrates the printability of various fiber sizes of type I collagen fiber ink, the range of collagen fiber content (w/v) of the ink, and the suitability of the nozzle diameter for each collagen-fiber ink printed at pH 7.2 at room temperature.

For both FIGS. 1 and 2, each printed 3D object contained two layers of printed ink. Each printed line of ink was separated by 1 mm gap for the purpose of ease of visualization of a defined structure.

FIGS. 1 and 2 also demonstrate that collagen content in the scaffold ranging from 9-23% could be easily printed in the range of pH from 4.8 to 7.2 using the nozzle diameter from 0.482 mm to 1.462 mm and fiber size from <50 μm to 125-150 μm. It is understood that collagen content higher than 25% can be achieved with fiber size larger than 150 μm and nozzle size greater than 1.436 mm.

The printed scaffold can be further mechanically reinforced while the scaffold was being printed. One example was demonstrated as follows.

5 g of purified type I collagen fibers was first swollen in 500 ml of 0.07M lactic acid. The swollen fibers were homogenized using a homogenizer (e.g., Silverson Homogenizer) to mechanically break down the fibers into fine fibrils. The homogenized fibrils were deaired and filtered through a 100 μm sieve. The filtered fibril dispersion was deaired and loaded into 100 cc syringe. The syringe was then attached to a pump to extrude the dispersion into 0.1 M NH$_4$OH bath to coacervate the collagen fibrils. The coacervated fibers were removed from the NH$_4$OH bath and dried in air. The dried filaments were then crosslinked with vapor HCHO generated from 2% HCHO solution overnight to stabilize the filaments. The filaments had an average diameter about 100 μm and an ultimate tensile strength about 0.1 kg.

10 The scaffold was mechanically reinforced by the following steps. The filament was first cut into the length of the dimension of the scaffold to be printed. Then a layer of the scaffold was printed, having 10 rows of ink adjacent to each other. A total of nine filaments were placed between each line of the printed rows. When the scaffold contained five layers, a total of 45 filaments were used to reinforce the overall scaffold. This mechanism can be applied to other geometries, such as the circular scaffolds and scaffolds having irregular dimensions.

One method to improve the cohesiveness of the printed object is to incorporate a low level of alginate (e.g., 0.5-1.0% w/v) into the ink and to spray the printed object with a low concentration of calcium chloride in the mist form to form ionic chelating bonds for 3D object stabilization.

Another method to improve the scaffold stability is to add gelatin methacryloyl to the ink by dissolving gelatin methacryloyl in the acetate solution (e.g., 1-3% w/v) prior to hydrating the microfibers. The printed 3D object is then subject to UV crosslinking with a photo-initiator.

The procedure above can be applied to pH 7.2. Since the isoelectric point of the collagen was at about pH 4.8, at pH 7.2 the particles would swell and imbibe more liquid into the intrafibrillar space. At this pH, the solid content per volume will decrease by about 10%. The decrease in solid content means a corresponding increase in pore size and pore volume of the printed 3D object.

When large fiber size ink is used in certain scaffold design, then a larger nozzle diameter can be used to meet the printing requirement (see FIGS. 1 and 2). The procedure is the same as that described for the small size fibers.

Characterization of the Printed Type I Collagen Fiber-Based Scaffolds

Gross Appearance from Light Microscopy

Figures 3A, 3B:
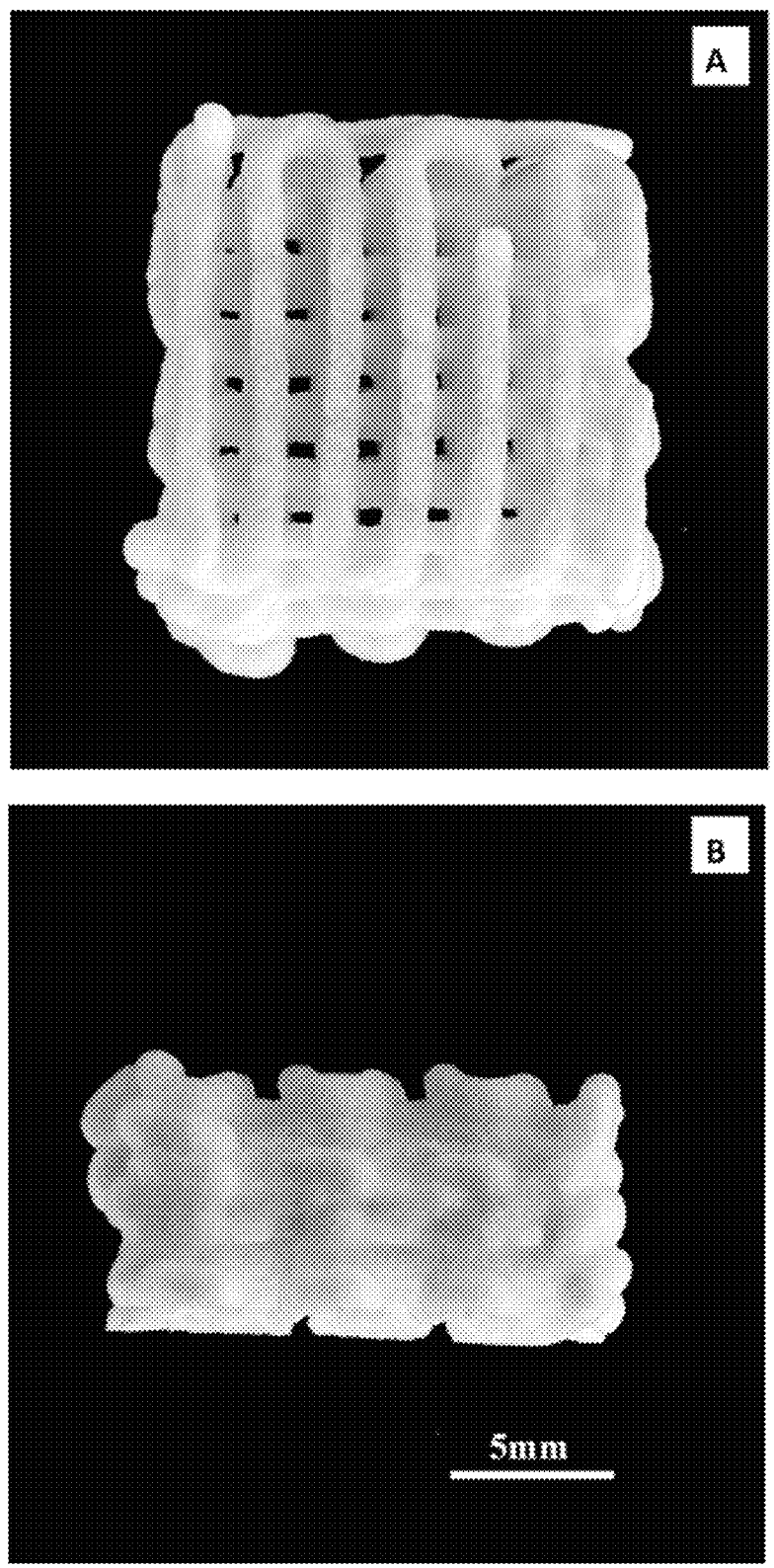
FIGS. 3A and 3B show the top view (FIG. 3A) and the side view (FIG. 3B) of multilayer scaffold printed with 125-150 μm fiber size and a 1.346 mm needle at pH 7.2 at room temperature.
Figure 4:
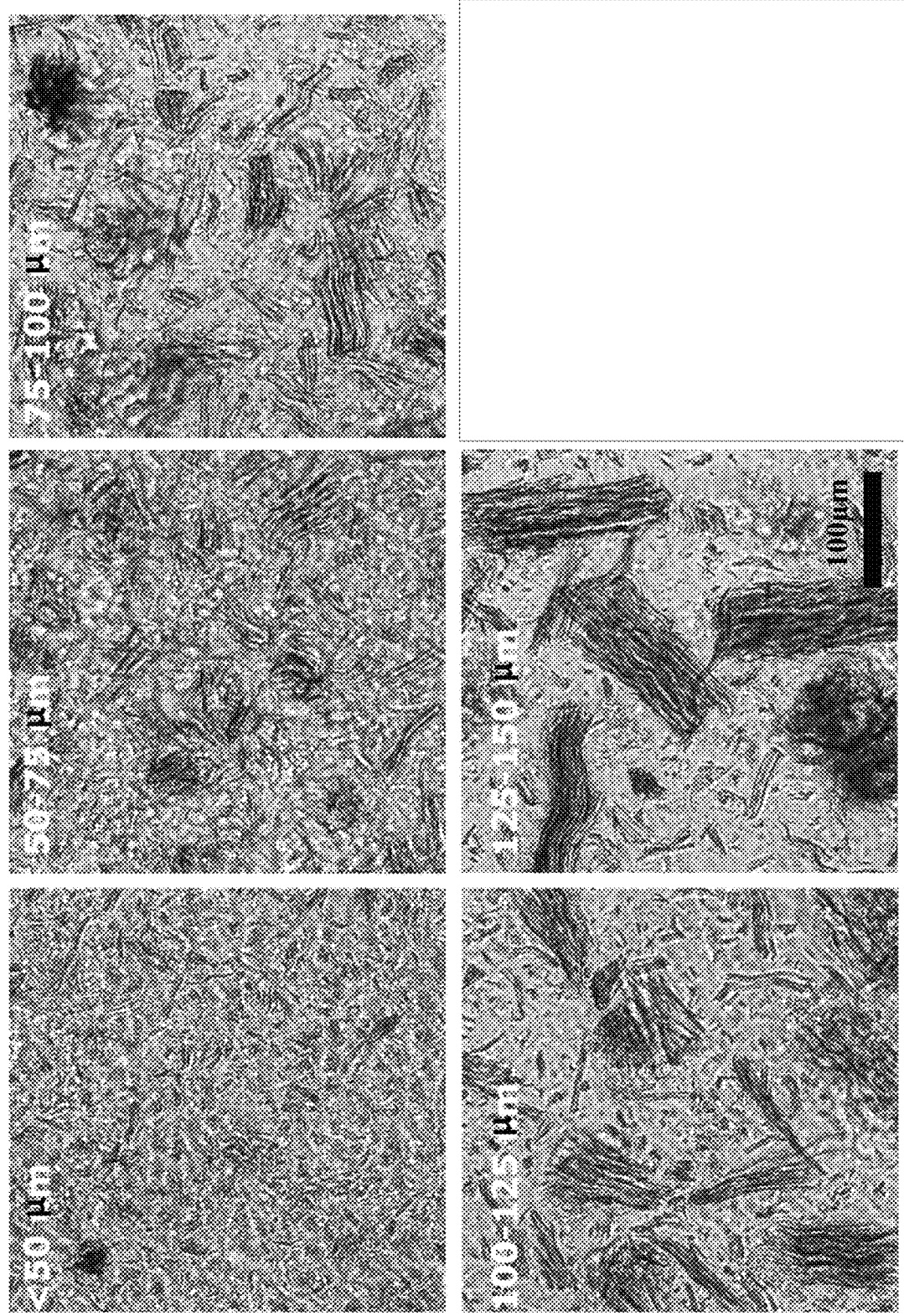
FIG. 4 shows light microscopic images of the native structure of the type I collagen micro-fibers at pH 7.2. All photos were taken at the same magnification. Scale bar indicates 100 μm.

Various printed 3D type I collagen fiber scaffolds are shown in FIGS. 1 and 2. Multiple layers of ink can be printed into a stable 3D structure without the need for an immediate post-printing stabilization step, such as adding gelatin methacryloyl material for UV crosslinking or alginate for calcium-based electrostatic bonding (FIG. 3). As type I collagen is the major component of the extracellular matrix (ECM) in all tissues and organs, the intact native structure of the type I collagen fibers in ink can serve important biological functions of the 3D scaffold (FIG. 4).

Morphology and Pore Structure by SEM

Figure 5A:
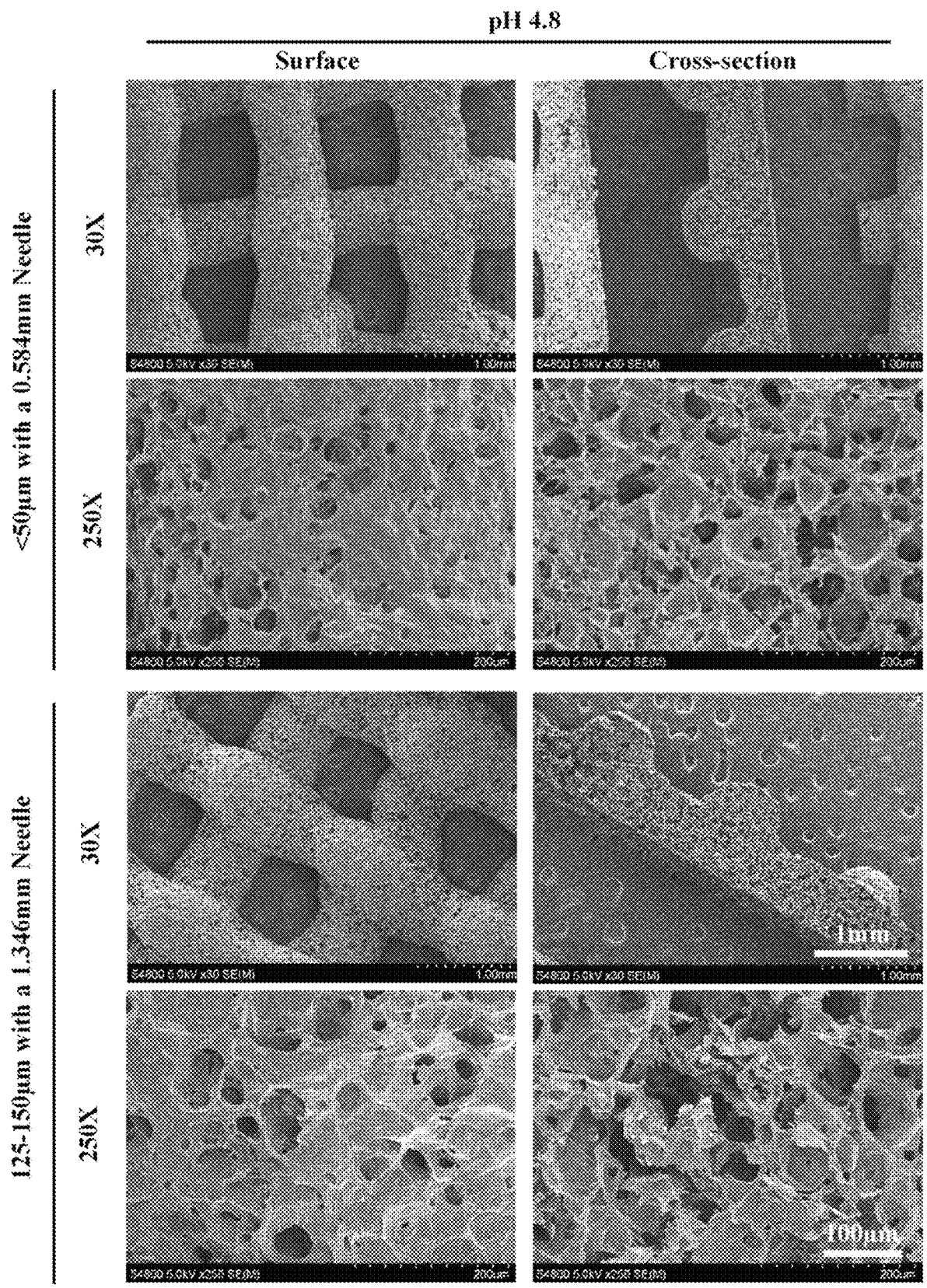
FIGS. 5A and 5B show the surface and cross-sectional SEM images for the <50 μm and 125-150 μm fiber printed scaffolds at pH 4.8 (FIG. 5A) and at pH 7.2 (FIG. 5B) at 30× and 250× magnifications.
Figure 5B:
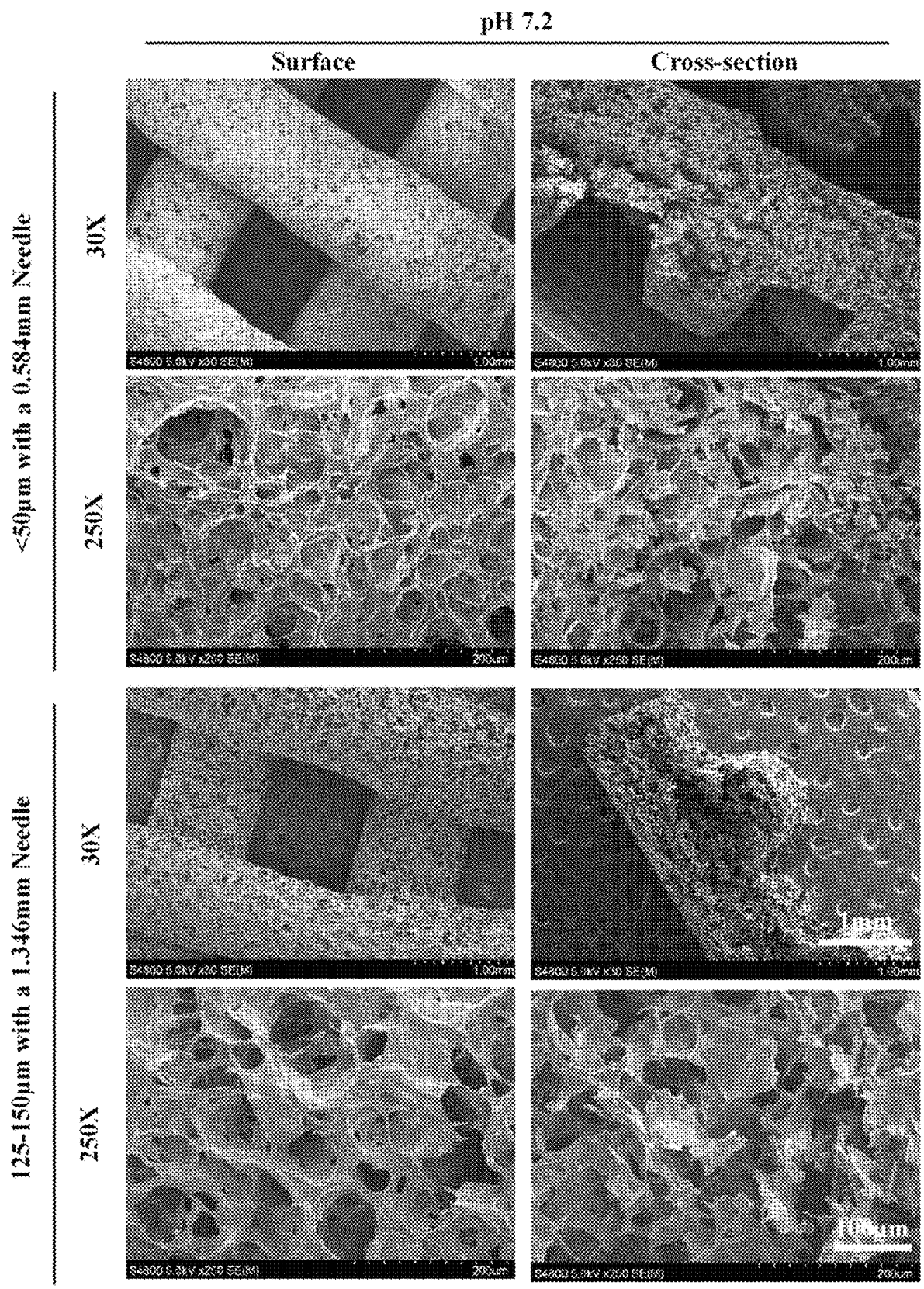

FIGS. 5A and 5B show the surface and cross-sectional view of the printed type 1 collagen fiber-based 3D scaffolds at pH 4.8 (FIG. 1) and pH 7.2 (FIG. 2) at different magnifications. The porous structure of the scaffolds is clearly demonstrated. In general, the pore sizes of the scaffold are sufficiently large for cell infiltration into the internal space of the printed structure for both pH conditions and for different fiber particle sizes.

Swelling Characteristics

Figure 6:
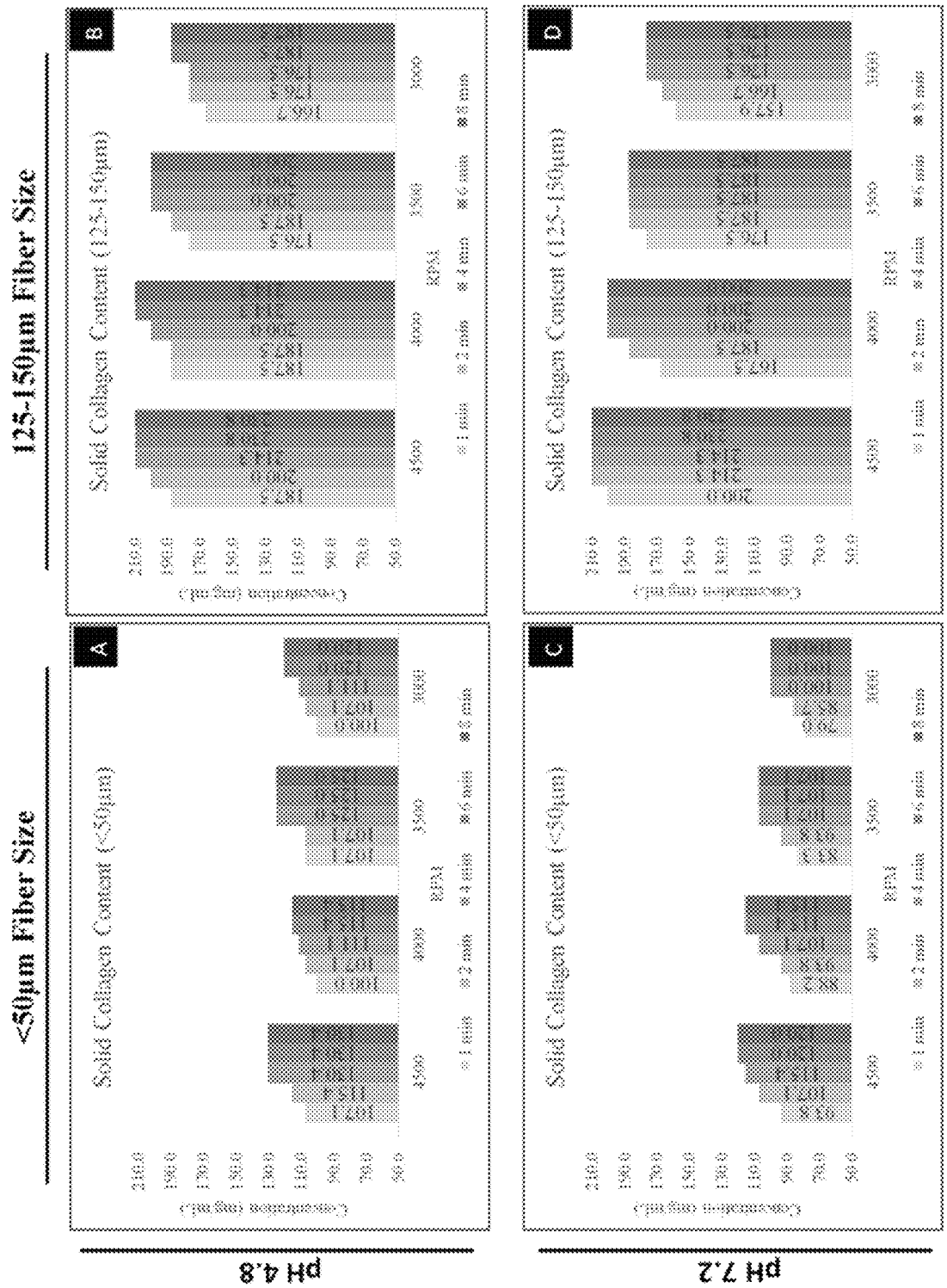
FIG. 6 shows the state of hydrated fiber-based inks at pH 4.8 and at pH 7.2 with various RPMs and times.

The swelling properties of the scaffolds are defined by the microfiber size and the pH of the buffer solution used in preparing the ink. Generally, the closer the pH of the buffer solution to the isoelectric point of the collagen, the higher the density or the lower the swelling of the printed scaffold will be. As shown in FIG. 6, for each microfiber size, upon hydration, it would take about 4-8 min to reach the state of equilibrium at a centrifugation speed of 3,000-4500 RPM (Universal 320 Centrifuge) for pH 4.8 and pH 7.2. Under the equilibrium hydration state, the hydrated particles behaved like toothpaste and flew smoothly out of the recommended printer nozzle. The solid content (weight/volume) can be calculated directly from the weight of collagen fibers and the final volume measured from the scaled centrifuge tube (mg/ml) and converted to the percentage of the solid collagen content in the ink. Even lower solid collagen content could result when the pH of the solution increases further, for example, to pH 11. Similarly, the microfibers would swell in acidic solutions such as lactic acid of pH 2.5.

It is important to emphasize that despite the significant mechanical disruption of the collagen fibers, the intact structure of the collagen fibers is maintained (FIG. 4).

Example 2. Preparation of a Type I Collagen Fiber Ink Containing Cells

Source of Adipose Tissue-Derived Stem Cells

Human adipose-derived stem cells (ADC) are purchased from ATCC. Cells were thawed and cultured in vitro until the number reached $1 \times 10^6$. A culture medium (Thermo Fisher) was used as the nutrient support during the preparation of the ink.

Preparation of Type I Collagen Fiber Ink Containing Cells

After cells were detached from the culture dish with trypsin and rinsed with culture medium, the cells were dispersed with 15 ml culture medium. About 1 g of the type I collagen microfibers (<50 μm) was slowly added to the cell-laden culture medium with mild agitation to fully hydrate the collagen fibers. The cells were uniformly incorporated within the collagen microfibers. Upon removal of extra culture medium from centrifugation, the ink containing cells was ready for printing.

Alternatively, $1 \times 10^6$ cells described above can be dispersed in 100 μl of culture medium and loaded onto a second nozzle. Cells were printed at the junctions of the closely printed lines at the end of each layer of collagen printing.

Example 3. Preparation of Type I Collagen Fiber Ink Containing Macromolecules

Two important families of natural macromolecules were tested to demonstrate the feasibility of incorporating these macromolecules into the type I collagen-based ink. One class of macromolecules is polysaccharides, including various glycosaminoglycans (GAGs). The other class of macromolecule is proteins, including fibronectins, growth factors, and other types of collagens. Some of these natural macromolecules are commercially available and can be purchased from Sigma Aldrich. These two families of macromolecules were used as examples to incorporate them into type I collagen fiber ink to form a type I collagen fiber ink containing natural macromolecules.

Most polysaccharide molecules and proteins are polyelectrolytic in nature. Therefore, they are soluble in aqueous solutions at a wide range of pH conditions. Within the range of biological function requirements, they were first dissolved in a fixed volume of buffer solution ranging from about pH 5 to about pH 7. A fixed weight of type I collagen fibers, according to the hydration capability of the fibers at different pH conditions (Example 1 and FIGS. 1 and 2), was then slowly added to an excess of the solution to fully hydrate the fibers and form an extrudable type I collagen fiber ink containing desired bioactive macromolecules. The exact final volume is dependent on the pH of the solution. The excess solution was removed via centrifugation. The ease of extrusion depends on the fiber size distribution and the diameter of the nozzle used for extrusion, according to the examples demonstrated in FIGS. 1 and 2 above.

Example 4. Preparation of Type I Collagen Fiber-Based Ink Containing Natural Carbonate Apatite Mineral Preparation of Natural Carbonate Apatite Mineral Particles Briefly, bovine femoral bone was collected from a local abattoir. After removing the adhering tissues, the bone was thoroughly cleaned and washed in water. The bone was dried, ground into small pieces, and treated in alcohol to remove the fat. The bone pieces were then deproteinated with hot 1M NaOH to hydrolyze the organic materials. The mineral particles were dried and further treated in an oven at 500-600° C. for a period of 24-48 hours to remove the residual organic materials.

The mineral particles were ground using the Spex Freeze/Mill under the liquid nitrogen temperature to various sizes of particles. The particle sizes between 10-150 μm were collected and sieved into sizes <50 μm, 50-75 μm, 75-100 μm, 100-125 μm, and 125-150 μm. For demonstration purpose, particle size <50 μm was used for the 3D printing application.

Figures 7A, 7B:
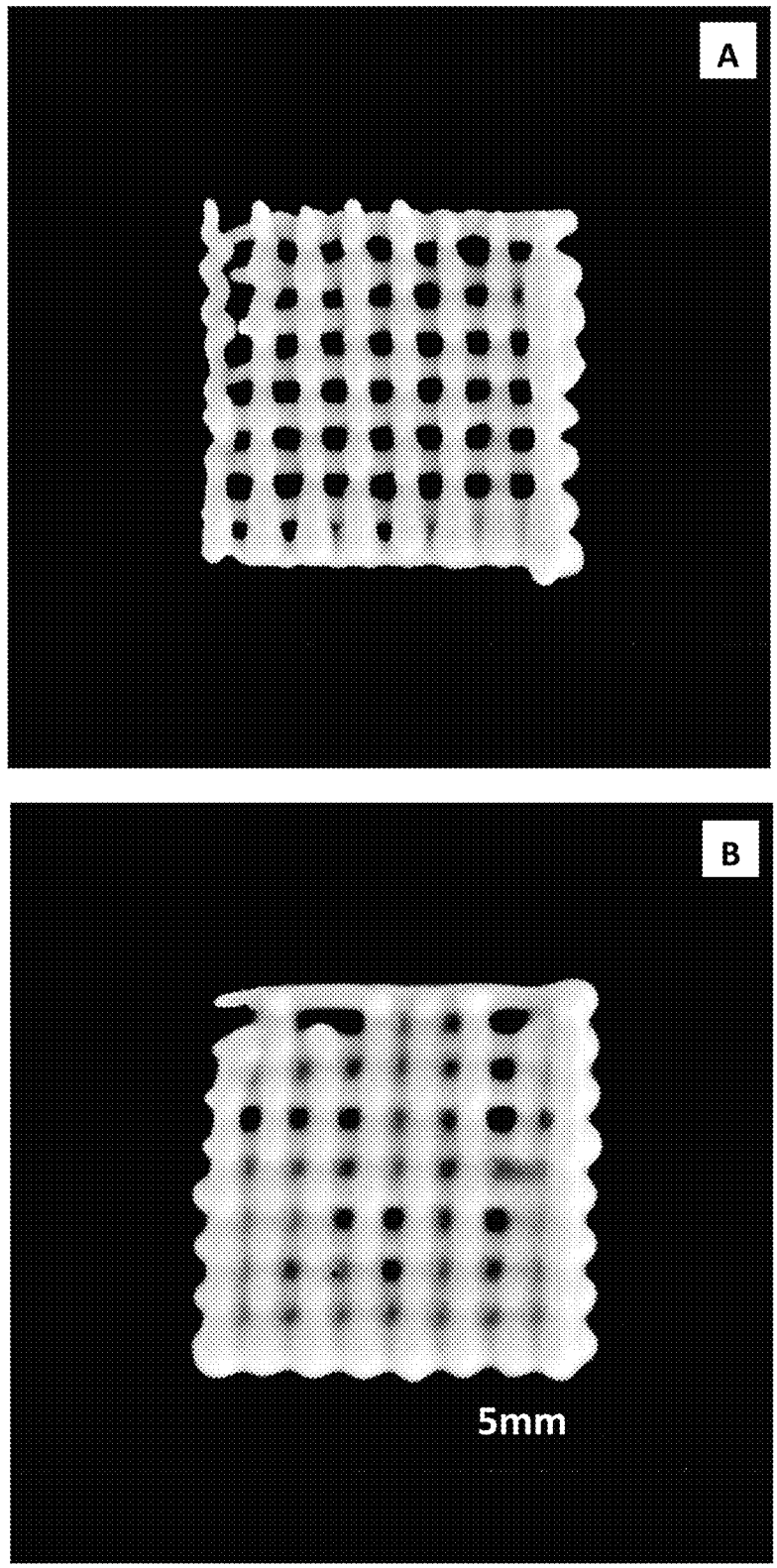
FIGS. 7A and 7B show a 3D Printed type I collagen-carbonate apatite scaffold with <50 μm particle size and a 0.584 mm needle at pH 4.8 at room temperature with a collagen apatite ratio of 80:20 (FIG. 7A) or with a collagen apatite ratio of 60:40 (FIG. 7B).

Preparation of Type I Collagen Fiber-Based Ink Containing Natural Carbonate Apatite 0.8 g type I collagen fibers (<50 μm) are thoroughly mixed with 0.2 g carbonate apatite particles (<50 μm) at a ratio 80:20 (w/w) of collagen to mineral. The mixture is fully hydrated with sodium acetate buffer at pH 5. The excess buffer solution is removed, and the total volume of the ink is about 1.0 ml. FIG. 7 shows the 3D structure of the printed type I collagen-carbonate apatite scaffold.

Example 5. Preparation of Type II Collagen Fiber-Based Ink

Preparation of Purified Type II Collagen Fibers

Type II collagen fibers are prepared essentially as that described by FS Stevens and H Thomas (Biochem J. 135: 245-247, 1973). Briefly, bovine femoral heads were obtained from a local abattoir. After the adhering tissues were removed, the femoral heads were thoroughly washed in water. The articular cartilage was removed as thin slices with a scalpel. Cartilage slices (10 g wet wt.) were incubated with 600 ml of 3% $H_2O_2$ solution in the dark at 20° C. for 18 h with constant shaking, followed by repeated washing with water and with 1% (w/v) NaCl. The residual tissue was then digested with trypsin (twice crystallized) in 1% (w/v) $NaHCO_3$ (enzyme/tissue ratio approx. 1:100) for 18 h with constant shaking. After the tissue was washed repeatedly with water and 1% NaCl, the insoluble material was treated with 4% EDTA, pH 7.5, at 20° C. for 18 h to remove non-collagenous proteins. The tissue was then extracted with 0.1 M acetic acid three times, its pH was adjusted to 7.0, and it was finally washed with 1% NaCl. At this stage, the whole procedure was repeated, leaving a final product with the same dimensions as the original slices but consisting of type II collagen fibers only. The type II collagen fibers are dried.

Preparation of Type II Collagen Fiber-Based Ink

The procedure of preparing type II collagen fiber-based ink is essentially the same as the type I collagen fiber-based ink described in Example 1 above and further described below.

Purified type II collagen fibers were dried in a desiccator for 24 hrs. The dried fibers were then cut into small pieces with a mechanical knife cutter. 5 g of type II collagen fiber pieces were inserted into a polycarbonate sample vial (Spex Freezer/Mill) which contains a stainless-steel impactor and two end plugs. The sample vial was then slotted into the dual electromagnetic grinder chamber. The chamber was immersed in the liquid nitrogen bath. The solidified collagen fibers were subjected to the electromagnetic force that impacts the type II collagen fibers via the steel impactor to reduce the fibers into microscopic fibers without inducing thermal degradation. With control of time, generally 4-10 minutes, various fiber sizes between 10 μm to 150 μm are obtained.

The microfibers are then sieved to produce several size groups, including fiber sizes <50 μm, 50-75 μm, 75-100 μm, 100-125 μm, and 125-150 μm. Fiber size less than 50 μm were used as an example for the preparation of type II collagen fiber-based ink to print 3D scaffolds using a nozzle of 0.584 mm diameter as follows.

1.4 g of the type II collagen fibers was hydrated in 15 ml of sodium phosphate buffer at pH 7.2. Upon hydration of the fibers, the excess liquid was removed by centrifugation. The total volume was around 10 ml. Taking the density of collagen to be 1.41 g/ml, the volume occupied by collagen would be around 1 ml. Therefore, the solid collagen content in the hydrated ink was about 14% (w/v). Similar to type I collagen, the hydrated type II collagen fibers have physical properties similar to toothpaste.

Since the ink contains significant solid content, the printed type II collagen scaffold can be removed from the printer for further processing without the need to perform any steps of scaffold stabilization post printing. The printed scaffold was then subjected to freeze-drying to remove the water from the scaffold without altering the size or shape of the scaffold. A subsequent chemical crosslinking was applied to stabilize the scaffold for in vivo stability. All other applications applicable to type I collagen fiber-based ink described in the above examples can be applied to type II collagen.

Example 6. Preparation of Decellularized Extracellular Matrix (dECM) Inks

Preparation of Decellularized Tissue Matrix

Articular cartilage was used as an example for the preparation of dECM with the aim to preserve as much as possible the ECM matrix materials without retaining any cell-related moieties, including cell debris, DNAs, and RNAs, to render the material biocompatible and non-immunogenic. The procedure to prepare a decellularized articular cartilage ECM is described as follows.

Briefly, bovine femoral heads were obtained from a local abattoir. After removing the adhering tissues and thoroughly washing in water, articular cartilage was removed as thin slices with a scalpel. The cartilage slices were subjected to the following treatments: The tissue slices were subjected to three freeze-thaw cycles to break down cell membranes for easy extraction of cell-related moieties, including cell debris, released DNAs, and RNAs. Liquid nitrogen was used to freeze the tissue to reduce the processing time. The tissue was then washed extensively with water and 1% (w/v) NaCl to remove the cell-related moieties. The tissue was next treated with alcohol (isopropanol) (1 g/50 ml) for 24 h under constant agitation to remove lipids. The tissue was then treated with 0.1% SDS (1 g/100 ml) for 12 h at room temperature to remove residual lipids. Upon washing in water, the tissue was treated with DNase (50 U/ml) and RNase (1 U/ml) each for 3 h at room temperature under constant agitation to completely remove the DNA and RNA from the tissue. Finally, the tissue was washed with three times of purified water (1 g/200 ml) followed by twice with 1% NaCl (1 g/100 ml). The above procedure is a rather mild treatment. It retains at least 50% of the important matrix proteoglycans and all the type II collagen in the matrix for their biological functions. The decellularized articular cartilage matrix was freeze-dried and stored.

Preparation of Decellularized Articular Cartilage Ink

The method of preparing the articular cartilage dECM ink is similar to that described for the type I collagen fiber-based ink in Example 1. Briefly, 5 g dECM of articular cartilage prepared above was subjected to the freeze/milling process described in Example 1. Again, the particle size <50 µm was used as an example for the ink preparation. As the matrix contains a high content of glycosaminoglycan (GAG) moieties, therefore, it contains a high number of negative charge groups derived from sulfate and carboxyl groups. To maintain a high solid content in the ink, the acetate buffer at a pH in the range of 4.2-4.7 was used. Thus, 1 g dECM microfiber matrix was hydrated in 20 ml of acetate buffer at pH 4.5. The excess buffer was removed via centrifugation, leaving a toothpaste-like ink for bio-printing applications.

It is noted that the composition of the dECM matrix from different batches can be adjusted by adding exogenous components of GAGs or bioactive proteins to produce a more consistent composition of the ink for tissue engineering research and applications.

The present disclosure is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A collagen fiber-based ink for bioprinting, comprising a dispersion of solid collagen fiber particles in an aqueous phase, wherein the collagen fiber particles are at a concentration between 12% (w/v) and 25% (w/v), and wherein the collagen fiber particles have from about 240 moles of negative charges/mole collagen to about 240 moles positive charges/mole collagen, and wherein the collagen fiber-based ink has a pH of about 4.8.

2. The collagen fiber-based ink of claim 1, wherein the collagen fiber particles have an average particle size of from about 10 µm to about 150 µm.

3. The collagen fiber-based ink of claim 1, wherein the pH is the pI of the collagen fiber particles.

4. The collagen fiber-based ink of claim 1, comprising one or more of the following features:
   wherein the collagen fiber-based ink is adapted to print a three-dimensional (3D) structure using a nozzle having a diameter of from about 0.4 mm to about 2 mm;
   wherein the aqueous phase comprises water or a saline solution;
   wherein the collagen fiber particles are not enzyme-treated or acid-treated;
   wherein the collagen fiber particles do not contain atelocollagen or soluble intact collagen with telopeptides;
   wherein the collagen fiber particles comprise type I collagen, type II collagen, type III collagen, genetically engineered equivalents thereof, or a combination thereof;
   wherein the collagen fiber particles comprise type I collagen;
   wherein the collagen fiber particles comprise type II collagen;
   wherein the collagen fiber-based ink comprises a cell;
   wherein the cell comprises a differentiated tissue specific cell;
   wherein the cell comprises an undifferentiated stem cell;
   wherein the collagen fiber-based ink comprises a macromolecule;
   wherein the collagen fiber-based ink comprises a mineral;
   wherein the collagen fiber-based ink comprises a decellularized collagen-rich tissue.

5. The collagen fiber-based ink of claim 4, wherein the 3D structure or the collagen fiber-based ink comprises an extracellular matrix (ECM).

6. The collagen fiber-based ink of claim 4, wherein the macromolecule comprises a growth factor, a cytokine, alginate, cellulose, agarose, chitosan, glycosaminoglycan, fibronectin, laminin, elastin, fibrin, gelatin, gelatin methacryloyl, collagen methacryloyl, a synthetic polymer, or a combination thereof.

7. The collagen fiber-based ink of claim 4, wherein the mineral comprises hydroxyapatite, carbonate apatite, tricalcium phosphate, calcium sulfate, or a combination thereof.

8. The collagen fiber-based ink of claim 4, wherein the decellularized collagen-rich tissue is derived from skin, bone, cartilage, tendon, ligament, muscle, nerve, liver, or blood vessel.

9. A kit comprising the collagen fiber-based ink of claim 1.

10. A method of preparing the collagen fiber-based ink of claim 1 comprising:
    a) obtaining purified collagen fibers from a collagen-rich tissue;
    b) comminuting the purified collagen fiber into collagen fiber particles having have an average particle size of from about 10 µm to about 150 µm; and
    c) hydrating the collagen fiber particles to pH about 4.8 with a solution to form an extrudable collagen fiber-based ink comprising collagen fiber particles at a concentration of from 12% (w/v) to 25% (w/v).

11. A collagen fiber-based ink prepared by the method of claim 10.

12. A method of printing a 3D structure, comprising extruding the collagen fiber-based ink of claim 1 with a bioprinter or a 3D printer.

13. A method of printing a 3D structure, comprising:
    a) obtaining purified collagen fibers from a collagen-rich tissue;
    b) comminuting the purified collagen fiber into collagen fiber particles having an average particle size of from about 10 µm to about 150 µm;
    c) hydrating the collagen fiber particles to pH about 4.8 with a solution to form an extrudable collagen fiber-based ink comprising collagen fiber particles at a concentration of 12% (w/v) to 25% (w/v); and
    d) extruding the collagen fiber-based ink with a bioprinter or a 3D printer to print the 3D structure.

14. The method of claim 12, comprising one or more of the following features:

wherein the 3D printer is an inkjet printer, a robotic dispensing printer, a mechanical extrusion printer, or a laser-based printer;

wherein the bioprinter or 3D printer comprises a nozzle having a diameter of from about 0.4 mm to about 2 mm;

wherein the 3D structure comprises an ECM;

wherein the ECM formed immediately after printing has a solid content substantially identical to native tissue.

15. A 3D structure formed according to the method of claim 12.

16. The 3D structure of claim 15, comprising one or more of the following features:

wherein the collagen fiber particles do not contain atelocollagen or soluble intact collagen with telopeptides;

wherein the collagen fiber particles comprise type I collagen, type II collagen, type III collagen, genetically engineered equivalents thereof, or a combination thereof;

comprising collagen fiber particles at a concentration of from 12% (w/v) to 25% (w/v);

wherein the collagen fiber particles have an average particle size of from about 10 μm to about 150 μm;

comprising an ECM;

further comprising an additional component; or wherein the additional component comprises a cell, a macromolecule, a mineral, a decellularized collagen-rich tissue, or a combination thereof.

* * * * *